United States Patent [19]

Schon et al.

[11] 4,183,909
[45] Jan. 15, 1980

[54] PHENYLGLYCINE-CONTAINING NEW PEPTIDES WITH GASTRINE EFFECTS AND A PROCESS FOR THE PREPARATION THEREOF

[75] Inventors: Istvan Schon; Lajos Kisfaludy, both of Budapest; Vince Varro, Szeged; Laszlo Varga, Szeged; Jozsef Nafradi, Budapest, all of Hungary

[73] Assignee: Richter Gedeon Vegyeszeti Gyar Rt., Budapest, Hungary

[21] Appl. No.: 859,931

[22] Filed: Dec. 12, 1977

[30] Foreign Application Priority Data

Dec. 24, 1976 [HU] Hungary ............................... RI 607

[51] Int. Cl.$^2$ ..................... A61K 29/00; A61K 37/00; C07C 103/52
[52] U.S. Cl. ........................................ 424/9; 424/177; 260/112.5 R
[58] Field of Search ................ 260/112.5 R; 424/177, 424/9

[56] References Cited

U.S. PATENT DOCUMENTS 3,896,103  7/1975  Hardy et al. .................. 260/112.5 R

OTHER PUBLICATIONS

J. C. Anderson et al., J. Chem. Soc. L 108 (1967).
O. B. Smirnov et al., Khimia Pirodnykh Soedenii I. 94 (1971).
M. Portelli et al., Il Farmaco Ed. Sc. 28, 322, (1973).
J. M. Davey et al., J. Chem. Soc. (555 1066).
J. S. Morley et al., Proc. Roy. Soc. 170B 97 (1978).
E. Wunsch et al., Z. Physiol. Chem. 353 1246 (1977).
J. S. Morley et al., J. Chem. Soc. C 522, 726, 910, 809 (1978).
G. W. Kenner et al., J. Chem. Soc. C 762 (1968).
A. von Dungen et al., Liebigs Ann. Chem. 1976, 860.

*Primary Examiner*—Delbert R. Phillips
*Attorney, Agent, or Firm*—Karl F. Ross

[57] ABSTRACT

The invention relates to novel peptides of formula (I),

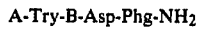 (I)

wherein
A is tert.-butoxycarbonyl-aminooxy-acyl, benzyloxycarbonyl-aminooxy-acyl, (aminooxy)-acyl or E-aminooxy-acyl, wherein E is benzoyl or straight-chained or branched $C_{1-5}$ aliphatic acyl, and
B represents methionyl, leucyl, norleucyl, norvalyl or 2-amino-decanoyl, or acid addition salts or complexes thereof. The novel compounds according to the invention exert gastrin effects and can be applied to advantage in the diagnostics and therapy. The novel compounds of formula (I) are prepared according to the invention by reacting a tetrapeptideamide of formula (II),

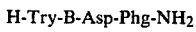 (II)

wherein B is as defined above, with an (aminooxy)-acyl containing compound of the general formula $A_1$-X, wherein
$A_1$ has the same meanings as A with the exception of the (aminooxy)-acyl, and
X is hydroxy group, halogen, pivaloyloxy, a group of the formula R—O—$CO_2$— (wherein R is lower alkyl, phenoxy which can have a nitro substituent or one or more halogen or N-succinimidoxy.

16 Claims, No Drawings

PHENYLGLYCINE-CONTAINING NEW PEPTIDES WITH GASTRINE EFFECTS AND A PROCESS FOR THE PREPARATION THEREOF

The invention relates to phenylglycine-containing new peptides with gastrin effects and pharmaceutical compositions containing the same, furthermore to a process for the preparation thereof.

The new peptides according to the invention correspond to formula (I),

A-Trp-B-Asp-Phg-NH$_2$     (I)

wherein

A is tert.-butoxycarbonylamino-oxy-acyl, benzyloxycarbonylamino-oxy-acyl, (aminooxy)-acyl or E-aminooxy-acyl, wherein E is benzoyl or a straight-chained or branched C$_{1-5}$ aliphatic acyl, preferably formyl, acetyl or pivaloyl, and B is methionyl, leucyl, norleucyl, norvalyl or 2-aminodecanoyl.

The phenylglycyl group, indicated as "Phg" in formula (I), is always of L or D configuration.

The acid addition salts and complexes of the above peptides are also within the scope of the invention.

The term "acyl", used in connection with the definition of substituent A, is preferably lower aliphatic acyl, particularly acetyl or propionyl.

As known, the biologically active center of gastrin, a peptide hormone consisting of 17 amino acids which stimulates gastric acid secretion, is the carboxy-terminal tetrapeptide-amide of the formula H-Trp-Met-Asp-Phe-NH$_2$. The gastric acid secretion stimulating effect of this tetrapeptide-amide is lower by about one order of magnitude than that of the total hormone. Several methods are known to synthetise the tetrapeptide-amide H-Trp-Met-Asp-Phe-NH$_2$ [J. C. Anderson et al.: J. Chem. Soc. C 108 (1967); Smirnov et al.: Khimia prirodnykh soedinenii 7, 94 (1971); Portelli, M. and Renzi, G.; Borin, G. E.: Il Farmaco Ed. Sci. 28, 322 (1973); J. M. Davey et al.: J. Chem. Soc. C 555 (1966); Hungarian patent specification No. 153,299; M. Dabrowska et al.: Roczniki Chemii 46, 1295 (1972)]. More than hundred analogs and substituted derivatives of the above tetrapeptide-amide have also been described [J. M. Davey et al.: J. Chem. Soc. C 555 (1966); J. S. Morley: Proc. Roy. Soc. 170B, 97 (1968); M. Portelli and G. Renzi: Il Farmaco Ed. Sci. 28, 316 (1973); Hungarian patent specification No. 153,375]. Of these compounds the pentapeptide-amide of the formula BOC-$\beta$-Ala-Trp-Met-Asp-Phe-NH$_2$, the most active derivative, is available under the name "pentagastrin" and is applied as a diagnostic agent in the determination of the maximum gastric acid secretion ability.

Several analogs of pentagastrin and the above tetrapeptide-amide have been described, in which some of the amino acids were replaced by others [J. Morley: Proc. Roy. Soc. 170B, 97 (1968); E. Wünsch and K.-H. Deimer: Hoppe-Seyler's Z. Physiol. Chem. 353, 1246 (1972); Merley et al.: J. Chem. Soc. C 522, 726, 910, 809, 715 (1968); Kenner et al.: J. Chem. Soc. C 762 (1968); A. von Dungen et al.: Liebigs Ann. Chem. 860 (1976); Japanese patent specification No. 71 17,234; Japanese patent specification No. 16,743/1971]. All of these compounds are, however, less active than pentagastrin.

It is known that peptides containing $\alpha$-(aminooxy)-carboxylic acids resist the effects of numerous proteolytic enzymes [L. Kisfaludy, M. Löw, T. Dévényi: Acta. Biochim. Biophys. Acad. Sci. Hung. 6, 393 (1971)]. Thus e.g. the protracted effects of ACTH analogues containing an $\alpha$-(aminooxy)-carboxylic acid on the terminal amino group can be attributed presumably to the fact that the $\alpha$-(aminooxy)-acyl group protects the molecule against the attack of aminopeptidase type enzymes (Hungarian patent specification No. 167,655).

Now it has been found that pentagastrin analogs containing an $\alpha$-(aminooxy)-carboxylic acid on the terminal amino group are very active compounds; the activities of the (aminooxy)-acetyl, $\alpha$-L- and -D-(aminooxy)-propionyl and $\beta$-(aminooxy)-propionyl derivatives are particularly remarkable. Some of these derivatives are more active than pentagastrin itself.

The new compounds of formula (I) can be prepared according to the invention by reacting a compound of the formula (II),

H-Trp-B-Asp-Phg-NH$_2$     (II)

wherein B is as defined above, with a compound containing an (aminooxy)-acyl group and having the formula A$_1$-X, wherein A$_1$ has the same meaning as A with the exception of the (aminooxy)-acyl group, and X is hydroxy, halogen (preferably chlorine, pivaloyloxy, a group of the formula R—O—CO$_2$— (wherein R is lower alkyl, preferably ethyl or isobutyl, a phenoxy which can have a nitro substituent or one or more halogen substituents) (preferably p-nitrophenoxy, 2,4,6-trichlorophenoxy, 2,3,5-trichlorophenoxy, pentachlorophenoxy or pentafluorophenoxy group) or N-succinimidoxy group.

When a compound of the formula A$_1$-X, wherein X is hydroxy, is used as a reactant, the acylation is performed preferably in the presence of dicyclohexyl carbodiimide.

If desired, a compound of formula (I) is converted into its pharmaceutically acceptable acid addition salt or complex, or a salt is converted into another pharmaceutically acceptable salt or inner salt, or a free compound of formula (I) is liberated from its salt.

The preferred reactants of the formula A$_1$-X are mixed anhydrides or active esters formed with pivaloic acid or a carbonic acid-hemiester. Of the latter compounds the halogenated phenylesters, primarily the pentachlorophenyl and pentafluorophenyl esters, are particularly preferred.

The tetrapeptide-amides of the formula H-Trp-B-Asp-Phg-NH$_2$, used as starting substances, can be prepared by fragment condensation or stepwise condensation according to methods known in the art. Of these methods e.g. the azide, mixed anhydride, dicyclohexyl carbodiimide and activated ester methods are to be mentioned.

If necessary, the functional groups not participating in the reaction are protected with appropriate blocking groups. Of the blocking groups, those which can be removed by hydrolysis, acidolysis or catalytic hydrogenation are the most preferred. Carboxy groups can be protected, e.g. by esterifying with benzylalcohol, tert.-butanol and p-chloro-benzylalcohol, whereas formyl, tosyl, trityl, trifluoroacetyl, o-nitrosulfenyl, phthalyl and p-chloro-carbobenzoxy groups, particularly carbobenzoxy and tert.-butoxycarbonyl groups, can be used to protect aminooxy and amino groups. The nitrogen atom of the indole skeleton of tryptophan can be protected with the formyl group.

By the proper selection of the blocking groups compounds can be prepared which can be deblocked in a single step, or from which the blocking groups can be split off selectively by methods known in the art, such as hydrolysis, acidolysis, catalytic hydrogenation, etc.

According to a preferred method of the invention the pentahalophenyl ester method is applied to introduce the protected N-terminal (aminooxy)-acyl group into the molecule. In this instance the active ester is reacted with the C-terminal H-Trp-B-Asp-Phg-NH$_2$. This latter compound is prepared from Z-L-Phg-OH or Z-D-Phg-OH, by converting it first into Z-L-Phg-NH$_2$ or Z-D-Phg-NH$_2$ by methods known in the art. Thereafter the protecting group is split off and the C-terminal tetrapeptide-amide (H-Trp-B-Asp-D-Phg-NH$_2$ or H-Trp-B-Asp-L-Phg-NH$_2$) is built up stepwise, using the appropriate protected amino acid-(N-hydroxysuccinimide)-esters or -(pentahalophenyl)-esters. The Z blocking group is removed with hydrogen bromide in glacial acetic acid or by catalytic hydrogenation. Instead of the Z blocking group, a BOC group can be applied as well, this latter group can be removed by treatment with an acid under less severe conditions.

The ester bond protecting the β-carboxy group of aspartic acid can be split off selectively in the dipeptide, tripeptide or tetrapeptide stage. This blocking group can also be split off along with the amino blocking group by acidolysis or by catalytic hydrogenolysis.

The end-products can be purified by simple recrystallization, precipitation, column chromatography on silica gel or ion exchange chromatography on carboxymethyl cellulose.

Depending on their methods of preparation, the new compounds are obtained either as free acids or in the form of salts. The salts formed with organic or mineral acids can be converted into inner salts either by methods known per se or as a result of the purifying procedure.

The biological activities of the new compounds according to the invention were tested by the methods of Ghosh and Schild (Br. J. Pharmac. Chemoth. 13, 54 1958) and Lai (Gut 5, 327 1964), modified by Pissidis and Clark (Gut 8, 196 1967). The pharmacological tests have shown that the new compounds, when administered intravenously, increase the gastric acid secretion to a great extent. It is particularly remarkable that the new compounds, in contrast with pentagastrin, are resorbed also from the small intestines, and, when administered in a dosage of 20 μg/100 g body weight, are sometimes more effective than pentagastrin administered in an intravenous dosage of 0.2 μg/100 g. It is worth noting here that pentagastrin does not increase the gastric acid secretion when administered enterally even in higher dosages. It is also remarkable that some of the new compounds highly increase the gastric acid secretion after resorption from the rectum. Taking into account that the new compounds are active after resorption from the small intestines and rectum, and are sometimes more active than pentagastrin, they can be applied in a new and advantageous manner in diagnosis and therapy.

The activity and resorption data of the new compounds according to the invention are summarized in Table 1.

Table 1

Gastric acid secretion increasing effects of the new compounds, administered enterally or parenterally, in comparison with that of a 0.2 μg/100 g i.v. dosage of pentagastrin

| Compound | | | 0.2 μg | 2.0 μg | 20 μg | 20 μg |
|---|---|---|---|---|---|---|
| A | B | Phg | i.v. | i.v. | intestinal | rectal |
| BOC-OGly | Met | D | 28 | 50 | — | — |
| BOC-OGly | Leu | D | — | — | — | 60 |
| BOC-OGly | Met | L | — | 116 | 124 | 38 |
| BOC-OGly | Leu | L | — | — | — | 17 |
| BOC-D-OAla | Met | D | 36 | — | — | 22 |
| BOC-D-OAla | Leu | D | 45 | — | 146 | 41 |
| BOC-D-OAla | Met | L | 180 | — | — | — |
| BOC-D-OAla | Leu | L | — | — | 48 | 43 |

The term "pharmaceutically acceptable complexes" refers to compounds of the novel peptides formed with certain organic or mineral substances, which impart protracted effects to the peptides. Of the organic substances e.g. certain gelatine types, carboxymethyl celluloses, alginic acid esters, poly(floretine)phosphate, amino acid polymers or other polymers and copolymers are to be mentioned. Of the inorganic substances hyroxides and relatively insoluble salts (such as phosphates and pyrophosphates) of certain metals (such as zinc) can be used. The above effect can also be attained with certain silicates, which form water-insoluble complexes with the new peptides, the structures of which are not yet elucidated.

The new peptides according to the invention, furthermore their salts and complexes, can be converted into pharmaceutical compositions for enteral or parenteral administration. These compositions may contain, beside the active agent, organic or mineral carriers, diluents and/or auxiliary agents applicable in the pharmaceutical industry. The pharmaceutical compositions may be e.g. solid, freeze-dried substances containing a compound non-reacting with peptide (such as a carbohydrate) as carrier, or concentrated or dilute suspensions or emulsions, which may also contain inert preservatives and/or stabilizing agents.

The pharmaceutical compositions according to the invention can be applied as diagnostic agents in the determination of the maximum gastric acid secretion. They can also be applied in the therapy of patients with decreased or no gastric acid secretion. The new compositions can be applied to advantage in the treatment of praeatrophic gastritis and subacid complaints. Since pentagastrin exerts a trophic effect favoring the recovery of mucous membrane, the new compositions can also be used to advantage in the treatment of disorders connected with atrophic processes of the mucous membrane of the stomach.

The invention is elucidated in detail by the aid of the following non-limiting Examples. The abbreviations used in the Examples correspond to those applied in the literature (J. Biol. Chem. 247, 977/1972). Further abbreviations are as follows:

OGly: α-(aminooxy)-acetic acid
OAla: α-(aminooxy)-propionic acid
DCC: dicyclohexyl carbodiimide
PCPOH: pentachlorophenol
PFPOH: pentafluorophenol
SuOH: N-hydroxy-succinimide
DMF: dimethyl formamide
HMFA: hexamethylphosphoric acid triamide The melting points were determined on a Dr. Tottoli type (Büchi) apparatus. The thin layer chromatograms were prepared on silica gel layers (Kieselgel G) prepared according to Stahl, and the following solvent mixtures were used as eluting agents:
1. chloroform:methanol—95:5
2. chloroform:methanol—9:1
3. chloroform:n-hexane:acetic acid—8:1:1
4. ethyl acetate:P-AA-W—9:1
5. ethyl acetate:P-AA-W—8:2
6. ethyl acetate:P-AA-W—7:3
7. ethyl acetate:P-AA-W—3:2
8. ethyl acetate:P-AA-W—1:1
9. ethyl acetate:P-AA-W—2:3
10. ethyl acetate:P-AA-W—85:15

The symbol P-AA-W represents a 20:6:11 mixture of pyridine, acetic acid and water.

The thin layer chromatograms were developed with ninhydrin solution. The chromatographic sheets were sprayed with ninhydrin solution, dried at 105° C. for about 5 minutes, subjected to chlorine gas, vented, and finally treated with o-toluidine-potassium iodide solution.

The column chromatographic purification of the substances was performed with silica gel (Kieselgel G), particle size: 62–200 μm.

EXAMPLE 1

Step 1 N-(Benzyloxycarbonyl)-D-phenylglycine-amide 11.6 ml (84 mmoles) of triethylamine are added to a solution of 24.0 g (84 mmoles) of Z-D-Phg-OH in 170 ml of chloroform, and 8.9 ml (84 mmoles) of ethyl chlorocarbonate are added dropwise to the mixture at $-10°$ C. The solution of the mixed anhydride is stirred for additional 10 minutes at $-10°$ C., thereafter cooling is stopped, and gaseous ammonia is introduced into the mixture for one hour. Next day the reaction mixture is evaporated in vacuo, and the solid residue is isolated with water. The crude product is crystallized from ethanol. 11.8 g (49.4%) of Z-D-Phg-NH$_2$ are obtained; the chromatographically uniform substance melts at 171°–173° C. $R_f^4$: 0.75, $[\alpha]_D = -76.8°$ (c=1.0, in dimethyl formamide).

Analysis: Calculated for $C_{16}H_{16}O_3N_2$ (M.wt.: 284.30): C: 67.59%, H: 5.67%, N: 9.85%. Fpund: C: 67.43%, H: 5.70%, N: 9.98%.

Step 2 D-Phenylglycine-amide hydrobromide 20.0 g (70 mmoles) of Z-D-Phg-NH$_2$, prepared as described in Step 1, are dissolved in 40 ml of acetic acid, and 70 ml of a 8 n HBr solution in acetic acid are poured to the solution. After 1 hour the reaction mixture is diluted with ether and the hydrobromide is filtered off. The salt, containing a great excess of HBr, is recrystallized from a tenfold amount of ethanol. 14.15 g (87.5%) of H-D-Phg-NH$_2$.HBr are obtained; m.p.: 263.0°–263.5° C. (determined on a Koffler apparatus). $R_f^8$ (HBr): 0.25; $R_f^8$ base: 0.40. $[\alpha]_D = -75.6°$ (c=1.0, in dimethyl formamide).

Analysis: Calculated for $C_8H_{10}ON_2Br$ (M.wt.: 231.10): C: 41.60%, H: 4.77%, N: 12.13%. Found: C: 41.40%, H: 4.82%, N: 12.01%.

STEP 3
N-(Benzyloxycarbonyl)-L-aspartyl-β-(tert.-butyl ester)-D-phenylglycine-amide 6.31 g of Z-Asp (O$^t$Bu)-OSu, 3.89 g (16.8 mmoles) of H-D-Phg-NH$_2$.HBr (prepared as described in Example 1, Step 2) and 2.10 ml (15 mmoles) of triethylamine are reacted with each other in a suspension formed with 150 ml of chloroform. Next day the thick suspension is evaporated in vacuo and the residue is recrystallized from ethanol. 5.02 g (73.6%) of Z-Asp-(O$^t$Bu)-D-Phg-NH$_2$ are obtained; the chromatographically uniform substance melts at 179°–181° C. A sample of the substance, recrystallized from ethyl acetate, melts at 188°–189° C. $R_f^4 = 0.75$; $[\alpha]_D = -59.5°$ (c=1.0, in dimethyl formamide).

Analysis: Calculated for $C_{24}H_{29}O_6N_3$ (M.wt.: 455.50): C: 63.28%, H: 6.42%, N: 9.23%. Found: C: 63.22%, H: 6.60%, N: 8.96%.

Step 4 L-Aspartyl-β-(tert.-butyl ester)-D-phenylglycine-amide hydrochloride 12.83 g (28.2 mmoles) of Z-Asp(O$^t$Bu)-D-Phg-NH$_2$, prepared as described in Example 1, Step 3, are dissolved in 200 ml of DMF, and 2.46 ml (28.2 mmoles) of concentrated hydrochloric acid and 2 g of palladium-on-carbon catalyst are added to the cooled solution. Gaseous hydrogen is bubbled through the resulting suspension for 2.5 hours under stirring. The catalyst is filtered off, the filtrate is evaporated, the residue is dissolved in ethanol, and the solution is decolourized. Ethanol is evaporated in vacuo, and the residue is triturated with ether. 10.0 g (99%) of H-Asp(O$^t$Bu)-D-Phg-NH$_2$.HCl are obtained; the chromatographically uniform substance melts at 169°–170° C. $R_f^4 = 0.15$.

Step 5
N-(tert.-Butoxycarbonyl)-L-methionyl-L-aspartyl-β-(tert.-butyl ester)-D-phenylglycine-amide 5.0 g (14 mmoles) of H-Asp(O$^t$Bu)-D-Phg-NH$_2$.HCl, prepared as described in Example 1, Step 4, and 4.85 g (14 mmoles) of BOC-Met-OSu are dissolved in 60 ml of DMF, and 1.96 ml (14 mmoles) of triethylamine are added to the solution. Next day the resulting suspension is evaporated in vacuo, and the residue is isolated with water. The obtained crude product, weighing 7.83 g, is decolourized in 40 ml of hot ethanol, and 40 ml of water are added to the hot solution to precipitate the product. 6.57 g (84%) of BOC-Met-Asp(O$^t$Bu)-D-Phg-NH$_2$ are obtained; the chromatographically uniform product melts at 194°–196° C. A sample of the product melts at 197°–198° C. after recrystallization from ethanol. $R_f^4 = 0.75$; $[\alpha]_D = -67.2°$ (c=1.0, in dimethyl formamide).

Analysis: Calculated for $C_{26}H_{40}O_7N_4S$ (M.wt.: 552.69): C: 56.51%; H: 7.30%, N: 10.14%, S: 5.78%. Found: C: 56.81%, H: 7.34%, N: 9.98%, S: 5.69%.

Step 6 L-Methionyl-L-aspartyl-D-phenylglycine-amide hydrochloride 5.6 g (10.1 mmoles) of BOC-Met-Asp(O$^t$Bu)-D-Phg-NH$_2$, prepared as described in Example 1, Step 5, are dissolved in 10 ml of acetic acid, and 3.5 ml (35 mmoles) of mercaptoethanol and 50 ml of 4 n hydrochloric acid in acetic acid are poured into the solution. After 30 minutes the reaction mixture is evaporated in vacuo, and the solid residue is isolated with dry ether. 4.84 g of H-Met-Asp-D-Phg-NH$_2$.HCl ($R_f^7 = 0.1$), containing an excess of hydrochloric acid, are obtained. The resulting product is used in the next step without purification.

Step 7
N-(tert.-Butoxycarbonyl)-L-tryptophyl-L-methionyl-L-aspartyl-D-phenylglycine-amide 4.4 g (10.2 mmoles) of H-Met-Asp-D-Phg-$NH_2$.HCl, prepared as described in Example 1, Step 6, and 4.10 g (10.2 mmoles) of BOC-Trp-OSu are dissolved in 100 ml of dimethyl formamide, and 2.85 ml (20.4 mmoles) of triethylamine are added to the solution. Next day the resulting suspension is evaporated in vacuo, and the residue is isolated with water. 6.66 g (95.8%) of BOC-Trp-Met-As-D-Phg-$NH_2$ are obtained; m.p.: 216°–218° C. (decomposition). A sample of the product is recrystallized from 80% ethanol. The resulting substance decomposes at 222° C.; $R_f{}^5$=0.3, $[\alpha]_D$= −65.5° (c=1.0, in dimethyl formamide).

Analysis: Calculated for $C_{33}H_{42}O_8N_6S$ (M.wt.: 682.81): C: 58.05%, H: 6.20%, N: 12.31%, S: 4.68%. Found: C: 58.23%, H: 6.30%, N: 12.60%, S: 4.86%.

Step 8
L-Tryptophyl-L-methionyl-L-aspartyl-D-phenylglycine amide 6.0 g (88.8 mmoles) of BOC-Trp-Met-Asp-D-Phg-$NH_2$, prepared as described in Example 1, Step 7, are treated with 60 ml of a dioxane solution of hydrochloric acid in the presence of 3.1 ml (44 mmoles) of mercaptoethanol. After 15 minutes the reaction mixture is diluted with dry ether, and the separated solids are filtered off. The resulting 6.23 g. of hydrochloride, containing a large excess of hydrochloric acid, is suspended in 150 ml of water, the suspension is neutralized (pH=7) with triethylamine, stirred, and the precipitate is filtered off and washed with water. 4.0 g (78%) of H-Trp-Met-Asp-D-Phg-$NH_2$ are obtained; m.p.: 230°–232° C. (decomposition); $R_f{}^7$=0.3.

Step 9 Pentachlorophenyl tert.-butoxycarbonyl-aminooxy-acetate 8.0 g (41.8 mmoles) of BOC-OGly-OH and 11.1 g (42.0 mmoles) of pentachlorophenol are dissolved in 160 ml of dry dioxane, the solution is cooled to a temperature below 5° C., and 8.6 g (42.0 mmoles) of dicyclohexyl carbodiimide (DCC) are added. The reaction mixture is allowed to stand at room temperature overnight, and then the saturated dicyclohexyl urea (DCU) is filtered off. The filtrate is evaporated in vacuo, and the solid residue is recrystallized from a mixture of dioxane and ethanol. 13.7 g (74.3%) of BOC-OGly-OPCP are obtained: m.p.: 167°–168° C., $R_f{}^3$=0.7.

Analysis: Calculated for $C_{13}H_{12}O_5NCl_5$ (M.wt.: 439.510): C: 35.52%, H: 2.75%, N: 3.18%, Cl: 40.33%. Found: C: 35.37%, H: 2.90%, N: 3.31%, Cl: 40.12%.

Step 10
2-(tert.-Butoxycarbonyl-aminooxy)-acetyl-L-tryptophyl-L-methionyl-L-aspartyl-D-phenylglycine-amide 1.50 g (2.57 mmoles) of H-Trp-Met-Asp-D-Phg-$NH_2$, prepared as described in Example 1, Step 8, are suspended in 15 ml of dimethyl formamide, and 2.26 ml (5.14 mmoles) of triethylamine and 1.20 g (2.73 mmoles) of BOC-OGly-OPCP, prepared as described in Example 1, Step 9, are added to the suspension. The suspension is stirred until the solids dissolve, and then the mixture is allowed to stand overnight. The reaction mixture is evaporated and the residue is triturated with ether. 2.12 g (an amount higher than the theoretical one) of the crude product are obtained. The crude product is dissolved in a small amount of solvent mixture 5, the solution is poured onto a column containing 20 g of silica gel, and the column is eluted with solvent mixtures 5 [elution rate: 15 ml/hour]. The pure fractions are recrystallized twice from 20 ml of 80% ethanol. 0.82 g (41.4%) of BOC-OGly-Trp-Met-Asp-D-Phg-$NH_2$ are obtained; m.p.: 199°–200° C. (decomposition), $R_f{}^4$=0.15, $R_f{}^5$=0.40, $[\alpha]_D$= −40.3° (c=1.0, in dimethyl formamide).

Analysis: Calculated for $C_{35}H_{45}O_{10}N_7S$ (M.wt.: 755.86): C: 55.62%, H: 6.00%, N: 12.97%, S: 4.24%. Found: C: 55.91%, H: 6.18%, N: 13.35%, S: 4.16%.

EXAMPLE 2

Step 1 N-(Benzyloxycarbonyl)-L-phenylglycine-amide 27.6 g (97 mmoles) of Z-L-Phg-OH are dissolved in 300 ml of dry tetrahydrofuran, and 13.55 ml (97 mmoles) of triethylamine are added to the solution. The mixture is cooled to −10° C., and 12.1 ml (97 mmoles) of pivaloyl chloride are introduced. The suspension of the mixed anhydride is stirred for 10 minutes at −10° C., thereafter cooling is stopped and ammonia is bubbled through the suspension for one hour. Next day the reaction mixture is evaporated, and the residue is processed as described for the D enantiomer. 18.90 g (68.7%) of Z-L-Phg-$NH_2$ are obtained; m.p.: 172°–173° C., $R_f{}^4$=0.75, $[\alpha]_D$= +80.7° (c=1.0, in dimethyl formamide).

Step 2 L-Phenylglycine-amide hydrobromide

One proceeds as described in Example 1, Step 2, but Z-L-Phg-$NH_2$ is applied as starting substance. The title compound is obtained with a yield of 88.8%. $R_f{}^8$=0.25, $[\alpha]_D$= +76.5° (c=1.0, in dimethyl formamide).

Step 3 N-(Benzyloxycarbonyl)-L-aspartyl-β-(tert.-butyl ester)-L-phenylglycine-amide 8.65 g (37.5 mmoles) of H-L-Phg-$NH_2$.HBr, prepared as described in Example 2, Step 2, is reacted with 21.6 g (37.5 mmoles) of Z-Asp(O'Bu)-OPCP in 160 ml of DMF, in the presence of 5.15 ml (37.5 mmoles) of triethylamine. The suspension is stirred for 30 minutes, and then a further 5.15 ml (37.5 mmoles) portion of triethylamine is added. Next day the reaction mixture is evaporated in vacuo, and the oily residue is triturated with ether. The separated precipitate is washed with water, and the resulting 13.9 g of crude product is crystallized from aqueous ethanol. 10.6 g (65.8%) of Z-Asp(O'Bu)-L-Phg-$NH_2$ are obtained; the chromatographically uniform substance melts at 207°–208° C. A sample of the product is recrystallized from ethanol; this purified substance melts at 209° C. $R_f{}^4$=0.75, $[\alpha]_D$= +21.6° (c=1.57, in demethyl formamide).

Analysis: Calculated for $C_{24}H_{29}O_6N_3$ (M.wt.: 455.50): C: 63.28%, H: 6.42%, N: 9.23%. Found: C: 63.50%, H: 6.38%, N: 9.23%.

The precipitate, separated in a small amount from the etheral mother liquor of the crude product, is filtered off, washed with water and recrystallized from ethanol. 0.47 g (2.9%) of Z-Asp(O'Bu)-D-Phg-$NH_2$ are obtained; m.p.: 188°–189° C., $R_f{}^4$=0.75, $[\alpha]_D$=59.0° (c=1.0, in dimethyl formamide).

Step 4 L-Aspartyl-β(tert.-butyl ester)-L-phenylglycine-amide hydrochloride 9.6 g (21 mmoles) of Z-Asp/O'Bu)-L-Phg-$NH_2$, prepared as described in Example 3, are treated as indicated in Example 1, Step 4 to remove the protecting group. 8.03 g of H-Asp(O'Bu)-L-Phg-NH$_2$.HCl are obtained; the chromatographically uniform product (R$_f^4$=0.35) contains an excess of hydrochloric acid.

Step 5
N-(tert.-Butoxycarbonyl)-L-methionyl-L-aspartyl-β-(tert.-butyl ester)-L-phenylglycine-amide 3.95 g (10.5 mmoles) of H-Asp/O'Bu/-L-Phg-NH$_2$.HCl, prepared as described in Example 2, Step 4, and 5.22 g (12.6 mmoles) of BOC-Met-OPFP are dissolved in 50 ml of DMF, and 2.94 ml (21 mmoles) of triethylamine are added to the solution. After one hour the reaction mixture is evaporated in vacuo, the residue is isolated with n-hexane, and washed with water. The crude product, weighing 5.38 g, is dissolved in 25 ml of hot methanol, and the product is precipitated with 25 ml of water. 4.70 g (81%) of BOC-Met-Asp(O'Bu)-L-Phg-NH$_2$ are obtained. A sample of the product is purified by dissolving in methanol and precipitating with ether. The purified product melts at 162°–163° C., R$_f^4$=0.75, [α]$_D$=−5.5° (c=1.0, in dimethyl formamide).

Analysis: Calculated for C$_{26}$H$_{40}$O$_7$N$_4$S (M.wt.: 552.69): C: 56.51%, H: 7.30%, N: 10.14%, S: 5.7%. Found: C: 56.70%, H: 7.34%, N: 10.35%, S: 5.68%.

Step 6 L-Methionyl-L-aspartyl-L-phenylglycyl-amide hydrochloride 4.2 g (7.6 mmoles) of BOC-Met-Asp(O'Bu)-L-Phg-NH$_2$, prepared as described in Example 2, Step 5, are treated as described for the D isomer to obtain 3.2 g (97%) of H-Met-Asp-L-Phg-NH$_2$.HCl. The product melts at 198°–200° C.; R$_f^7$: 0.25 (see also that of the D isomer).

Step 7
N-(tert.-Butoxycarbonyl)-L-tryptophyl-L-methionyl-L-aspartyl-L-phenylglycyl-amide The process described in Example 1, Step 7 is repeated with the difference that 3.45 g (8 mmoles) of H-Met-Asp-L-Phg-NH$_2$.HCl, prepared as described in Example 2, Step 6, are used as starting substance. 4.77 g (97.9%) of BOC-Trp-Met-Asp-L-Phg-NH$_2$ are obtained; m.p.: 191°–193° C. (under decomposition). A sample of the product is recrystallized from 80% ethanol. The resulting purified product melts at 200° C. under decomposition; R$_f^5$: 0.35, [α]$_D$: 0° (c: 1.0, in dimethyl formamide).

Analysis: Calculated for C$_{33}$H$_{42}$O$_8$N$_6$S (M.wt.: 682.81): C: 58.05%, H: 6.20%, N: 12.31%, S: 4.68%. Found: C: 58.05%, H: 6.21%, N: 12.64%, S: 4.77%.

Step 8
L-Tryptophyl-L-methionyl-L-aspartyl-L-phenylglycine-amide

One proceeds as described in Example 1, Step 8, with the difference that 4.4 g (6.33 mmoles) of BOC-Trp-Met-Asp-L-Phg-NH$_2$, prepared as described in Example2, Step 7, are applied as starting substance. 2.90 g (76.5%) of H-Trp-Met-Asp-L-Phg-NH$_2$ are obtained, m.p.: 210° C. (decomposition), R$_f^7$: 0.30.

Step 9
2-(tert.-Butoxycarbonyl-aminooxy)-acetyl-L-tryptophyl-L-methionyl-L-aspartyl-L-phenylglycine-amide One proceeds as described in Example 1, Step 10, with the difference that 1.0 g (1.71 mmoles) of H-Trp-Met-Asp-L-Phg-NH$_2$ is applied as starting substance.

The starting substance is prepared as described in Example 2, Step 8. The crude product is purified by chromatography on a silica gel column, using solvent mixture 10 as eluting agent. 0.48 g (37.2%) of BOC-OGly-Trp-Met-Asp-L-Phg-NH$_2$ are obtained, m.p.: 169°–170° C. (decomposition), R$_f^5$: 0.35, [α]$_D$:+8.2° (c:1.0, in dimethyl formamide).

Analysis: Calculated for C$_{35}$H$_{45}$O$_{10}$N$_7$S (M.wt.:755.86): C: 55.62%, H: 6.00%, N: 12.97%, S: 4.24%. Found: C: 55.11%, H: 6.23%, N: 13.04%, S: 4.10%.

EXAMPLE 3

Step 1 2-(tert.-Butoxycarbonyl-aminooxy)-D-propionic acid pentachlorophenyl ester 4.10 g (20 mmoles) of BOC-D-Oala-OH and 5.32 g (20 mmoles) of pentachlorophenol are dissolved in 20 ml of dimethyl formamide, the solution is cooled to 0° C., and 4.12 g (20 mmoles) of DCC are added. The reaction mixture is stirred for 30 minutes at 0° C. and allowed to stand at room temperature overnight. The separated DCU is filtered off, the filtrate is evaporated in vacuo, the residue is triturated with dry ether, and the separated crystals are filtered off. The crude product, weighing 6.25 g, is recrystallized from ethanol. 5.80 g (64%) of BOC-D-OAla-OPCP are obtained; m.p.: 123°–124° C., R$_f^3$0.85, [α]$_D$:+68.95° (c:1.0, in dioxane).

Analysis: Calculated for C$_{14}$H$_{14}$O$_5$NCl$_5$ (M.wt.:453.537): C: 37.10%, H: 3.10%, Cl: 39.10%. Found: C: 37.16%, H: 3.92%, Cl: 39.01%.

Step 2
2-D-(tert.-Butoxycarbonyl-aminooxy)-propionyl-L-tryptophyl-L-methionyl-L-aspartyl-D-phenylglycyl-amide 1.50 g (2.57 mmoles) of H-Trp-Met-Asp-D-Phg-NH$_2$, prepared as described in Example 1, Step 8, are dissolved in 50 ml of DMF, and 2.26 ml (5.14 mmoles) of triethylamine and 1.24 g (2.73 mmoles) of BOC-D-OAla-OPCP, prepared as described in Example 3, Step 1, are added to the solution. After 5 hours of reaction the mixture is evaporated in vacuo, and the residue is triturated with ether. The crude product, weighing 1.90 g, is recrystallized from 100 ml of 96% ethanol. 1.06 g (53.5%) of BOC-D-OAla-Trp-Met-Asp-D-Phg-NH$_2$ are obtained; the chromatographically uniform product melts at 200°–204° C. under decomposition. R$_f^4$: 0.15, R$_f^5$: 0.30, [α]$_D$: −24.9° (c: 1.0, in dimethyl formamide).

Analysis: Calculated for C$_{36}$H$_{47}$O$_{10}$N$_7$S (M.wt.: 769.89): C: 56.16%, H: 6.15%, N: 12.74%, S: 4.16%. Found: C: 56.33%, H: 5.88%, N: 12.70%, S: 4.09%.

EXAMPLE 4

2-D-(tert.-Butoxycarbonyl-aminooxy)-propionyl-L-tryptophyl-L-methionyl-L-aspartyl-L-phenyl-glycineamide 1.0 g (1.71 mmoles) of H-Trp-Met-Asp-L-Phg-NH$_2$, prepared as described in Example 2, Step 8, is dissolved in 30 ml of DMF, and 0.24 ml (1.71 mmoles) of triethylamine and 0.85 g (1.88 mmoles) of BOC-D-OAla-OPCP, prepared as described in Example 3, Step 1, are added to the solution. Next day the reaction mixture is evaporated in vacuo, and the residue is triturated with dry ether. The crude product, weighing 1.45 g, are dissolved in a small amount of solvent mixture 10, the solution is poured onto a column filled with 100 g of silica gel, and the column is eluted at a rate of 15 ml/hour with solvent mixture 10. The pure fractions are combined, and the pure product is isolated. 0.74 g (56%) of BOC-D-OAla-Trp-Met-Asp-L-Phg-NH$_2$ are obtained; m.p.: 167°–168° C., R$_f^5$: 0.30, [α]$_D$: +29.8° (c: 1.0, in dimethyl formamide).

Analysis: Calculated for C$_{36}$H$_{47}$O$_{10}$N$_7$S (M.wt.: 769.89): C: 56.16%, H: 6.15%, N: 12.74%, S: 4.16%. Found: C: 56.40%, H: 6.31%, N: 12.65%, S: 4.01%.

EXAMPLE 5

Step 1
N-(Benzyloxycarbonyl)-L-leucyl-L-aspartyl-β-(tert.-butyl ester)-D-phenylglycine-amide 5.0 g (14.0 mmoles) of H-Asp(O$^t$Bu)-D-Phg-NH$_2$.HCl, prepared as described in Example 1, Step 4, and 5.13 g (14.2 mmoles) of Z-Leu-OSu are dissolved in 60 ml of DMF, and 1.96 ml (14.0 mmoles) of triethylamine are added to the solution. Next day the reaction mixture is evaporated in vacuo, and the residue is triturated with water. The resulting crude product, weighing 7.32 g, is recrystallized from ethanol under decolourizing. 6.05 g (77.7%) of Z-Leu-Asp(O$^t$Bu)-D-Phg-NH$_2$ are obtained; m.p.: 192°–194° C., R$_f^4$: 0.75. A sample of the product melts as 195°–196° C. after recrystallization from ethanol; [α9 $_D$: −69.5° (c: 1.0, in dimethyl formamide).

Analysis: Calculated for C$_{30}$H$_{40}$O$_7$N$_4$ (M.wt.: 568.67): C: 63.36%, H: 7.09%, N: 9.8%. Found: C: 63.54%, H: 7.38%, N: 10.07%.

Step 2 L-Leucyl-Laspartyl-D-phenylglycine-amide 5.20 g (9.15 mmoles) of Z-Leu-Asp(O$^t$Bu)-D-Phg-NH$_2$, prepared as described in Example 5, Step 1, are reacted with 50 ml of 1 n hydrogen bromide in acetic acid for one hour. The reaction mixture is evaporated in vacuo, and the hydrobromide is isolated with dry ether. The resulting 5.33 g of hydrobromide are suspended in 50 ml of chloroform, and the pH of the suspension is adjusted to 7 with triethylamine. The separated gelly product is filtered off and washed with ethanol. 2.45 g (70.5%) of H-Leu-Asp-D-Phg-NH$_2$ are obtained; m.p.: 218°–220° C., R$_f^7$:0.25.

Step 3
N-(tert.-Butoxycarbonyl)-L-tryptophyl-L-methionyl-L-aspartyl-D-phenylglycine-amide 2.25 g (5.93 mmoles) of H-Leu-Asp-D-Phg-NH$_2$, prepared as described in Example 5, Step 2, are dissolved in a mixture of 50 ml of DMF and 10 ml of HMFA, and 0.84 ml (5.93 mmoles) of triethylamine and 2.65 g (6.6 mmoles) of BOC-Trp-OSu are added to the solution. The reaction mixture is stirred for 4 hours, whereupon a clear mixture is obtained. The mixture is allowed to stand overnight, and then DMF is evaporated in vacuo. The residual mixture containing HMFA is diluted with water, the obtained suspension is allowed to stand at a cool place, and then the precipitate is filtered off. The resulting crude product, weighing 4.31 g, is boiled twice in ethyl acetate, and the suspension is filtered when hot. 2.87 g (72.8%) of BOC-Trp-Leu-Asp-D-Phg-NH$_2$ are obtained; m.p.: 195°–200° C., R$_f^5$: 0.55. The product is used in the next step without further purification.

Step 4
L-Tryptophyl-L-leucyl-L-aspartyl-D-phenylglycine-amide 2.8 g (4.2 mmoles) of BOC-Trp-Leu-Asp-D-Phg-NH$_2$, prepared as described in Example 5, Step 3, are treated with 30 ml of dioxane containing hydrochloric acid in the presence of 0.59 ml (8.4 mmoles) of mercaptoethanol. After 15 minutes the reaction mixture is diluted with dry ether. The separated hydrochloride, weighing 2.60 g, is suspended in 150 ml of water, and the pH of the suspension is adjusted to 7 triethylamine. The separated precipitate is filtered off and washed with water. 2.22 g (93.7%) of H-Trp-Leu-Asp-D-Phg-NH$_2$ are obtained; R$_f^7$: 0.35, m.p.: 246°–248° C. (decomposition).

Step 5
2-(tert.-Butoxycarbonyl-aminooxy)-acetyl-L-tryptophyl-L-leucyl-L-aspartyl-D-phenylglycine-amide 1.10 g (1.95 mmoles) of H-Trp-Leu-Asp-D-Phg-NH$_2$, prepared as described in Example 5, Step 4, are dissolved in 10 ml of DMF in the presence of 0.28 g (2.0 mmoles) of triethylamine, and 0.92 g (2.10 mmoles) of BOC-Ogly-OPCP, prepared as described in Example 1, Step 9, are added to the solution. Next day the reaction mixture is evaporated in vacuo and the residue is isolated with dry ether. The crude product, weighing 1.46 g, is admixed with tenfold amount of ethyl acetate, and the mixture is filtered when hot. The resulting substance, weighing 1.31 g, is dissolved in a small amount of solvent mixture 10, the solution is poured onto a column filled with 80 g of silica gel, and the column is eluted with solvent mixture 10 at a rate of 8 ml/hour. The pure fractions are combined and the product is isolated. The resulting product, weighing 0.52 g, is recrystallized from 80% ethanol. 0.45 g (31.3%) of BOC-OGly-Trp-Leu-Asp-D-Phg-NH$_2$ are obtained; m.p.: 206°–208° C. (6) , R$_f^6$: 0.75, [α]$_D$: −51.7° (c: 0.5, i dimethyl formamide).

Analysis: Calculated for C$_{36}$H$_{47}$O$_{10}$N$_7$ (M.wt.: 737.82): C: 58.60%; H: 6.42%, N: 13.29%. Found: C: 58.70%; H: 6.65%, N: 3.51%.

EXAMPLE 6

Step 1
N-(Benzyloxycarbonyl)-L-leucyl-L-aspartyl-β-(tert.-butyl ester)-L-phenylglycine-amide One proceeds as described in Example 5, Step 1, with the difference that 4.0 g (11.2 mmoles) of H-Asp(O$^t$Bu)-L-Phg-NH$_2$.HCl, prepared as described in Example 2, Step 4, are applied as starting substance. The crude product, weighing 5.42 g, is dissolved in ethanol, the solution is decolourized, and then the product is precipitated. 3.0 g (47 %) of Z-Leu-Asp(O$^t$Bu)-L-Phg-NH$_2$ are obtained; m.p.: 193°–194° C. (decomposition), R$_f^4$: 0.70, R$_f^2$: 0.65, [α]$_D$: 0° (c: 1.0, in dimethyl formamide).

Analysis: Calculated for C$_{30}$H$_{40}$O$_7$N$_4$ (M.wt.: 568.67): C: 63.36%, H: 7.09%, N: 9.85%. Found: C: 63.79%, H: 7.30%, N: 9.59%.

Step 2 L-Leucyl-L-aspartyl-β-(tert.-butyl ester)-L-phenyl-glycine-amide hydrochloride Gaseous hydrogen is bubbled through a mixture of 2.75 g (4.84 mmoles) of Z-Leu-Asp(O$^t$Bu)-L-Phg-NH$_2$, prepared as described in Example 6, Step 1, 50 ml of DMF, 0.45 ml (5.2 mmoles) of concentrated hydrochloric acid and 0.5 g of palladium-on-carbon catalyst. After 2 hours of reduction the catalyst is filtered off, and the filtrate is evaporated in vacuo. The residue is triturated with dry ether. 2.25 g (98.5%) of H-Leu-Asp(O$^t$BU)-L-Phg-NH$_2$.HCl are obtained; m.p.: 182°–183° C., R$_f^4$: 0.15.

Step 3 L-Leucyl-L-aspartyl-L-phenylglycine-amide hydrochloride 2.25 g (4.80 mmoles) of H-Leu-Asp(O$^t$Bu)-L-Phg-NH$_2$.HCl, prepared as described in Example 6, Step 2, are reacted with 20 ml of hydrochloric acid in acetic acid. After 40 minutes of reaction the mixture is evaporated in vacuo and the residue is triturated with ether. 2.0 g (99%) of H-Leu-Asp-L-Phg-NH$_2$. HCl are obtained; m.p.: 210° C. (decomposition), R$_f^7$: 0.20.

Step 4 N-(tert.-Butoxycarbonyl)-L-tryptophyl-L-methionyl-L-aspartyl-L-phenylglycine-amide 2.2 g (5.3 mmoles) of H-Leu-Asp-L-Phg-NH$_2$.HCl, prepared as described in Example 6, Step 3, are reacted with 2.32 g (5.8 mmoles) of BOC-Trp-OSu in 50 ml of DMF in the presence of 1.48 ml (10.6 mmoles) of triethylamine. Next day the reaction mixture is evaporated in vacuo and the residue is triturated with water. The obtained crude product, weighing 3.30 g, is crystallized from 70 ml of 80% ethanol under decolourizing. 2.30 g (65%) of BOC-Trp-Leu-Asp-L-Phg-NH$_2$ are obtained; m.p.: 205°–207° C. (decomposition), R$_f^5$: 0.40, [α]$_D$: −7.3° (c: 1.0, in dimethyl formamide).

Step 5 L-Tryptophyl-L-leucyl-L-aspartyl-L-phenylglycyl-amide 2.23 g (3.55 moles) of BOC-Trp-Leu-Asp-L-Phg-NH$_2$, prepared as described in Example 6, step 4, are treated with 25 ml of hydrochloric acid in dioxane in the presence of 0.47 ml (6.7 mmoles) of mercaptoethanol. After 10 minutes the mixture is diluted with dry ether, and the separated hydrochloride is isolated. The salt is suspended in water, the pH of the suspension is adjusted to 7 with triethylamine, then the precipitate is filtered off and washed with water. 1.16 g (61%) of H-Trp-Leu-Asp-L-PHg-NH$_2$ are obtained; m.p.: 214°–215° C. (decomposition), R$_f^7$: 0.40.

Step 6 2-(tert.-Butoxycarbonyl-aminooxy)-acetyl-L-tryptophyl-L-leucyl-L-aspartyl-L-phenylglycine-amide 0.57 g (1.0 mmole) of H-Trp-Leu-Asp-L-Phg-NH$_2$, prepared as described in Example 6, Step 5, and 0.48 g (1.1 mmoles) of BOC-OGly-OPCP, prepared as described in Example 1, Step 9, are dissolved in 15 ml of DMF, and 0.14 ml (1.0 mmole) of triethylamine are added to the solution. Next day the reaction mixture is evaporated in vacuo and the residue is triturated with ether. The resulting crude product, weighing 0.81 g, is purified as described for the D isomer. 0.30 g (40.5%) of BOC-OGly-Trp-Leu-Asp-L-Phg-NH$_2$ are obtained; m.p.: 196°–198° C. (decomposition), R$_f^5$: 0.35, [α]$_D$: 0° (c: 1.0, in dimethyl formamide).

Analysis: Calculated for C$_{36}$H$_{47}$O$_{10}$N$_7$ (M.wt.: 737.82): C: 58.60%, H: 6.42%, N: 13.29%. Found: C: 58.35%, H: 6.20%, N: 13.07%.

EXAMPLE 7 2-D-(tert.-Butoxycarbonyl-aminooxy)-propionyl-L-tryptophyl-L-leucyl-L-aspartyl-D-phenylglycine-amide 1.15 g (2.03 mmoles) of H-Trp-Leu-Asp-D-Phg-NH$_2$, prepared as described in Example 5, Step 4, are reacted with 1.0 g (2.2 mmoles) of BOC-D-OAla-OPCP, prepared as described in example 3, Step 1, in 10 ml of DMF in the presence of 0.29 ml (2.03 mmoles) of triethylamine. Next day the reaction mixture is evaporated in vacuo and the residue is triturated with ether. The obtained crude product, weighing 1.56 g, is recrystallized from 50 ml of 80% ethanol containing 0.3 ml 0.3 ml of acetic acid under decolourizing the mixture. 0.86 g (56%) of BOC-D-OAla-Trp-Leu-Asp-D-Phg-NH$_2$ are obtained; m.p.: 213°–214° C. (decomposition), R$_f^4$: 0.2, R$_f^5$: 0.4, [α]$_D$: −28.7° (c: 1.0, in dimethyl formamide).

Analysis: Calculated for C$_{37}$H$_{49}$O$_{10}$N$_7$ (M.wt.: 751.85): C: 59.11%, H: 6.57%, N: 13.04%. Found: C: 59.10%, H: 6.52%, N: 13.20%.

EXAMPLE 8 2-D-(tert.-Butoxycarbonyl-aminooxy)-propionyl-L-tryptophyl-L-leucyl-L-aspartyl-L-phenylglycine-amide 0.57 g (1.0 mmole) of H-Trp-Leu-Asp-L-Phg-NH$_2$, prepared as described in Example 6, Step 5, are reacted with 0.50 g (1.1 mmoles) of BOC-D-OAla-OPCP, prepared as described in Example 3, Step 1, in 15 ml of DMF in the presence of 0.14 ml (1.0 mmole) of triethylamine. Next day the reaction mixture is evaporated in vacuo and the crude product, weighing 0.77 g, is isolated with ether. The crude product is dissolved in a small amount of solvent mixture 10, the solution is poured onto a column filled with 30 g of silica gel, and the column is eluted with solvent mixture 10 at a rate of 5 ml/hour. The pure fractions are combined and the product is isolated. The obtained product, weighing 0.46 g, is dissolved in 10 ml of methanol and the solution is diluted with 70 ml of ether. 0.26 g (34.2%) of BOC-D-Oala-Trp-Leu-Asp-L-Phg-NH$_2$ are obtained; m.p.: 184°–185° C. (decomposition), R$_f^5$: 0.4, [α]$_D$: +18.8° (c: 1.0, in dimethyl formamide).

Analysis: Calculated for C$_{37}$H$_{49}$O$_{10}$N$_7$ (M.wt.: 751.83): C: 59.11%, H: 6.57%, N: 13.04%. Found: C: 58.92%, H: 6.40%, N: 12.88%.

EXAMPLE 9 step 1 N-tert.-Butoxycarbonyl-l-norleucine pentafluorophenyl ester 10.0 g (24.3 mmoles) of BOC-Nle-OH.DCHA are added to a mixture of 75 ml of ether and 25 ml of 2n aqueous sulfuric acid, and the mixture is shaken until the dissolution of the solid is complete. The phases are separated from each other, and the etheral solution is shaken again with 25 ml of 2n aqueous sulfuric acid and then with water. The etheral solution is evaporated in vacuo. The oily residue, weighing 5.44 is dissolved in 30 ml of ethyl acetate together with 4.42 g (24 mmoles) of pentafluorophenol, the solution is cooled to 0° C., and 4.63 g (22.5 mmoles) of dicyclohexyl carbodiimide are added. The resulting suspension is allowed to stand for 1 hour at a cool place, thereafter the solids are filtered off, and the filtrate is evaporated in vacuo. The residue is dissolved in 50 ml of n-hexane, and the solution is washed with 5×20 ml of 5% aqueous sodium hydrocarbonate solution and 2×20 ml of water. The organic solution is dried, evaporated in vacuo, and the oily residue is cooled to obtain a solid substance. 8.12 g (91%) of BOC-Nle-OPFP are obtained; m.p.: 55°–57° C., $[\alpha]_D$: −26.8° (c: 1.0, in dioxane), $R_f^2$: 0.80, $R_f^4$: 0.85.

Analysis: Calculated for $C_{17}H_{20}O_4NF_5$ (M.wt.: 397.35): C: 51.39%, H: 5.07%, F: 23.91%. Found: C: 51.51%, H: 4.68%, F: 24.66%.

Step 2 L-Aspartyl-(tert.-butyl ester)-D-phenylglycine-amide 10.6 g (23.2 mmoles) of Z-Asp(O'Bu)-D-Phg-NH₂, prepared as described in Example 1, Step 3, are suspended in 350 ml of methanol and 1.1 g of 10% palladium-on-carbon catalyst are added. Gaseous hydrogen is bubbled through the stirred suspension at atmospheric pressure. After 3 hours of reduction the suspension is filtered, the catalyst is washed with DMF in order to dissolve the product precipitated thereon, and the filtrate is evaporated in vacuo. The solid residue is crystallized from 100 ml of methanol. 5.5 g (74.0%) of H-Asp(O'Bu)-B-Phg-NH₂ are obtained; m.p.: 170°–171° C., $R_f^4$: 0.15.

Analysis:
Calculated for $C_{16}H_{23}N_4O_3$ (M.wt.: 321.28): C: 59.79%, H: 7.21%, N: 13.08%, Found: C, 59.80%, H: 7.10%, N: 13.18%,

Step 3
N-(tert.-Butoxycarbonyl)-L-norvalyl-L-aspartyl-β-(tert.-butyl ester)-D-phenylglycine-amide 1.60 g (5.0 mmoles) of H-Asp(O'Bu)-D-Phg-NH₂ are reacted with 1.99 g (5.0 mmoles) of BOC-Nle-OPFP in 10 ml of DMF in the presence of 0.70 ml (5.0 mmoles) of triethylamine. Next day the reaction mixture is evaporated in vacuo, the solid residue is admixed with ether, and the suspension is filtered. 2.45 g (91.9%) of BUC-Nle-Asp(O'Bu)-D-Phg-NH₂ are obtained; m.p.: 207°–208° C., $R_f^4$:0.75, $[\alpha]_D$:−62.8° (c: 1.0, in dimethyl formamide).

Analysis: Calculated for $C_{27}H_{42}O_7N_4$ (M.wt.: 534.64): C: 60.65%, H: 7.92%, N: 10.48%. Found: C: 60.63%, H: 8.04%, N: 10.18%.

Step 4 L-Norleucyl-L-aspartyl-D-phenylglycine-amide hydrochloride 2.20 g (4.11 mmoles) of BOC-Nle-Asp(O'Bu)-D-Phg-NH₂ are treated with 15 ml of 4 n hydrochloric acid in acetic acid. After 1 hour the reaction mixture is evaporated in vacuo, the solid residue is admixed with ether, and the suspension is filtered. 1.70 g (99%) of N-Nle-Asp-D-Phg-NH₂.HCl are obtained; m.p.: 225° C. (decomposition), $R_f^7$:0.20, $[\alpha]_D$:−63.7° (c:1.0, in dimethyl formamide).

Step 5
N-(tert.-Butoxycarbonyl)-L-tryptophyl-L-norleucyl-L-aspartyl-D-phenylglycine-amide 1.57 g (3.78 mmoles of H-Nle-Asp-D-Phg-NH₂.HCl are reacted with 1.52 g (3.78 mmoles) of BOC-Trp-OSu in 50 ml of DMF in the presence of 1.06 ml (7.6 mmoles) of triethylamine. Next day the reaction mixture is evaporated in vacuo, the residue is admixed with water, and the suspension is filtered. 2.45 g (97.5%) of BOC-Trp-Nle-Asp-D-Phg-NH₂ are obtained; m.p.: 217° C. (decomposition), $R_f^5$:0.35, $[\alpha]_D$−32.7° (c: 1.0, in dimethyl formamide).

Analysis: Calculated for $C_{34}H_{44}O_8N_6$ (M.wt.: 664.77): C: 61.43%, H: 6.67%, N: 12.64%. Found: C: 61.41%, H: 6.86%, N: 12.65%.

Step 6
L-Tryptophyl-L-norleucyl-L-aspartyl-D-phenylglycine-amide hydrochloride 2.20 g (3.32 mmoles) of BOC-Trp-Nle-Asp-D-Phg-NH₂ are treated with 25 ml of 4 n hydrochloric acid in dioxane in the presence of 1.20 ml (17 mmoles) of mercaptoethanol. After 15 minutes the solution is evaporated in vacuo, the residue is triturated with ether, and the solid is filtered off. 1.99 g (99.0%) of H-Trp-Nle-Asp-D-Phg-NH₂.HCl are obtained; m.p.: 217°–221° C. (decomposition), $R_f^7$:0.35, $[\alpha]_D$:−54.2° (c: 1.0, in dimethyl formamide).

Step 7
2-D-(tert.-Butoxycarbonyl-aminooxy)-propionyl-D-tryptophyl-L-norleucyl-L-aspartyl-D-phenylglycine-amide 1.80 g (3.0 mmoles) of H-Trp-Nle-Asp-D-Phg-NH₂.HCl are reacted with 1.36 g (3.0 mmoles) of BOC-D-OAla-OPCP, prepared as described in Example 3, Step 1, in 30 ml of DMF in the presence of 1.26 ml (9.0 mmoles) of triethylamine. Next day the reaction mixture is evaporated in vacuo, the residue is admixed with water, the solids are filtered off, and then chromatographed on a silica gel column in the usual way. 0.99 g of BOC-OAla-Trp-Nle-Asp-D-Phg-NH₂ are obtained; m.p.: 211°–212° C. (decomposition), $R_f^5$:0.35 $R_f^{10}$:0.25, $[\alpha]_D$:−22.8° (c: 1.0, in dimethyl formamide).

Analysis: Calculated for $C_{37}H_{49}O_{10}N_7$ (M.wt.: 751.85): C: 59.11%, H: 6.57%, N: 13.04%. Found: C: 59.10%, H: 6.30%, N: 13.21%.

EXAMPLE 10

Step 1 N-(tert.-Butoxycarbonyl)-N-norvaline pentafluorophenyl ester 8.0 g (20 mmoles) of BOC-Nva-OH.DCHA are added to a mixture of 60 ml of ether and 20 ml of 2 n aqueous sulfuric acid, and the mixture is shaken until the solid dissolves completely. The etheral phase is separated, washed with 20 ml of 2 n aqueous sulfuric acid and water, dried, and evaporated in vacuo. The oily residue is dissolved in 25 ml of ethyl acetate together with 3.70 g (20 mmoles) of pentafluorophenol, the solution is cooled to 0° C. 3.92 g (19 mmoles) of DCC are added, and the mixture is maintained at 0° C. for 1 hour. Thereafter the suspension is filtered, the filtrate is evaporated in vacuo, and the oily residue is dissolved in 50 ml of n-hexane. The organic solution is washed with 5×20 ml of 5% aqueous sodium hydrocarbonate solution and 2×20 ml of water and then evaporated in vacuo. The oily residue solidifies upon cooling. 6.21 g (81%) of BOC-Nva-OPFP are obtained, m.p.: 60°62° C., $R_f^3$:0.70, $[\alpha]_D$:−32.2° (c: 1.0, in dioxane).

Analysis: Calculated for $C_{16}H_{18}O_4NF_5$ (M.wt.: 383.32): C: 50.14%, H: 4.73%, F: 24.78%. Found: C: 50.06%, H: 4.64%, F: 24.63%.

Step 2
N-(tert.-Butoxycarbonyl)-L-norvalyl-L-aspartyl-β-(tert.-butyl ester)-D-phenylglycine-amide 1.60 g (5.0 mmoles) of H-Asp(O'Bu)-D-Phg-NH₂, prepared as described in Example 9, Step 2, are reacted with 1.91 g (5.0 mmoles) of BOC-Nva-OPFP in 10 ml of DMF in the presence of 0.70 ml (5 mmoles) of triethylamine. Next day the reaction mixture is evaporated in vacuo, the residue is admixed with ether, and the solids are filtered off. 2.36 g (87.4%) of BOC-Nva-Asp(O$^t$-Bu)-D-Phg-NH$_2$ are obtained; m.p.: 200°–202° C., R$_f^4$:0.75, [α]$_D$:−66.7° (c: 1.0, in dimethyl formamide).

Analysis: Calculated for C$_{26}$H$_{40}$O$_7$N$_4$ (M.wt.: 520.61): C: 59.98%, H: 7.74%, N:10.76%. Found: C: 60.08%, H: 7.68%, N: 10.96%

Step 3 L-Norvalyl-L-aspartyl-D-phenylglycine-amide hydrochloride 2.0 g (3.84 mmoles) of BOC-Nva-Asp-(O$^t$Bu)-D-Phg-NH$_2$ are treated with 15 ml of 4 n hydrochloric acid in acetic acid. After 1 hour the suspension is diluted with ether and filtered when cold, 1.52 g (98%) of H-Nva-Asp-D-Phg-NH$_2$.HCl are obtained; m.p.: 204° C. (decomposition), R$_f^7$:0.15, [α]$_D$:−58.0° (c: 1.0, in dimethyl formamide).

Step 4

N-(tert.-Butoxycarbonyl)-L-tryptophyl-L-norvalyl-L-aspartyl-D-phenylglycine-amide 1.50 g 1.50 g (3.74 mmoles) of H-Nva-Asp-D-Phg-NH$_2$.HCl are reacted with 1.50 g (3.74 mmoles) of BOC-Trp-OSu in 30 ml of DMF in the presence of 1.05 ml (7.5 mmoles) of triethylamine. Next day the reaction mixture is evaporated in vacuo, the residue is admixed with water, and the mixture is filtered. The obtained crude product, weighing 2.36 g, is recrystallized from 300 ml of 80% ethanol. 1.54 g (66.2%) of BOC-Trp-Nva-Asp-D-Phg-NH$_2$ are obtained; m.p.: 240° C. (decomposition), R$_f^5$:0.35, [α]$_D$:—60.5° (c: 1.0, in dimethyl formamide).

Analysis: Calculated for C$_{33}$H$_{42}$O$_8$N$_6$ (M.wt.: 650.71): C: 60.91%, H: 6.51%, N: 12.92%. Found: C: 60.66%, H: 6.59%, N: 12.57%.

Step 5

L-Tryptopbhyl-L-norvalyl-L-aspartyl-D-phenylglycine-amide hydrochloride 1.50 g (2.30 mmoles) of BOC-Trp-Nva-Asp-D-Phg-NH$_2$ are treated with 20 ml of 4 n hydrochloric acid in dioxane in the presence of 0.77 ml (11 moles) of mercaptoethanol. After 30 minutes the suspension is evaporated in vacuo, the solid residue is admixed with ether, and the suspension is filtered. 1.34 g (99.0%) of H-Trp-Nva-Asp-D-Phg-NH$_2$.HCl are obtained; m.p.: 216° C. (decomposition), R$_f^7$:0.30, [α]$_D$:−53.3° (c: 1.0, in dimethyl formamide).

Step 6

2-D-(tert.-Butoxycarbonyl-aminooxy)-propionyl-L-tryptophyl-L-norvalyl-L-aspartyl-D-phenylglycine-amide 1.24 g (2.11 mmoles) of H-Trp-Nva-Asp-D-Phg-NH$_2$.HCl are reacted with 0.95 g (2.10 mmoles) of BOC-D-OAla-OPCP in 40 ml of DMF in the presence of 0.88 ml (6.3 mmoles) of triethylamine. Next day the reaction mixture is evaporated in vacuo, the residue is admixed with water, filtered, and the precipitate is washed with water and ether. The crude product, weighing 1.40 g, is recrystallized from 7 ml of a 20:6:11 mixture of pyridine, acetic acid and water. 0.72 g of BOC-D-OAla-Trp-Nva-Asp-D-Phg-NH$_2$ are obtained; m.p.: 210° C., R$_f^5$:0.28, [α]$_D$:−26.5° (c: 1.0, in dimethyl formamide).

Analysis: Calculated for C$_{36}$H$_{47}$O$_{10}$N$_7$ (M.wt.: 737.79): C: 58.61%, H: 6.42%, N: 13.29%. Found: C: 58.57%, H: 6.20%, H: 13.17%.

EXAMPLE 11

Step 1

2-L-(tert.-Butoxycarbonylamino)-decanoic acid pentafluorophenyl ester 4.25 g (14.7 mmoles) of BOC-Ade-OH and 2.94 g (16.0 mmoles) of pentafluorophenol are dissolved in 40 ml of ethyl acetate and 2.99 g (14.5 mmoles) of DCC are added to the solution at 0° C. The reaction mixture is stirred for 1 hour at room temperature and for 1 hour at 0° C. The separated DCU is filtered off, the filtrate is evaporated in vacuo, and the oily residue is dissolved in 40 ml of n-hexane. The solution is washed with 5×20 ml of 5% aqueous sodium hydrocarbonate solution and 2×20 ml of water, dried, and evaporated in vacuo. The oily residue crystallizes upon cooling, 5.82 g (87.5%) of BOC-L-Ade-OPEF are obtained; m.p.: 45°–46° C., R$_f^2$: 0.85, [α]$_D$: −18.1° (c: 1.0, in dioxane).

Analysis: Calculated for C$_{21}$H$_{28}$O$_4$NF$_5$ (M.wt.: 434.45): C: 55.63%, H: 6.22%, F: 20.95%. Found: C: 55.96%, H: 5.96%, F: 20.89%.

Step 2

2-L-(tert.Butoxycarbonylamino)-decanoyl-L-aspartylβ(tert.butyl ester)-D-phenylglycine-amide 0.96 g (3.0 mmoles) of H-Asp)O$^t$Bu)-D-Phg-NH$_2$, prepared as described in Example 9, STep 2, are reacted with 1.36 g (3.0 mmoles) of BOC-L-Ade-OPFP in 10 ml of DMF in the presence of 0.42 ml (3.0 mmoles) of triethylamine. Next day the reaction mixture is evaporated in vacuo, the residue is triturated with ether, the suspension is filtered, and the precipitate is washed with ether. 1.53 g (86.4%) of BOC-L-Ade-Asp(O$^t$Bu)-D-Phg-NH$_2$are obtained; m.p.: 182°–183° C., R$_f^4$: 0.70, [α]$_D$: −27.6° (c: 1.0, in dimethyl formamide).

Analysis: Calculated for C$_{31}$H$_{50}$O$_7$N$_4$ (M.wt.: 590.89): C: 63.02%, H: 8.53%, N: 9.49%. Found: C: 62.89%, H: 8.66%, N: 9.44%.

Step 3

1-L-Amino-decanoyl-L-aspartyl-D-phenylglycine-amide hydrochloride 1.40 g (2.37 mmoles) of BOC-L-Ade-Asp(O$^t$Bu)-D-Phg-NH$_2$are treated with 15 ml of 4 n hydrochloric acid in acetic acid. After 1 hour the reaction mixture is evaporated in vacuo, the solid residue is admixed with ether, and the suspension is filtered. 1.0 g (89.3%) of H-L-Ade-Asp-D-Phg-NH$_2$.HCl is obtained; m.p.: 177°–178°

C., $R_f^7$: 0.35, $[\alpha]_D$: −58.9° (c: 1.0, in dimethyl formamide).

Step 4
N-(α-tert.-butoxycarbonyl-$N_{ind}$-formyl)-L-tryptophyl-2-L-amino-decanoyl-L-aspartyl-D-phenylglycine-amide 0.90 g (1.90 mmoles) of H-L-Ade-Asp-D-Phg-NH$_2$.HCl are reacted with 0.94 g of BOC-Trp(For)-OPFP in 15 ml of DMF in the presence of 0.53 ml (3.8 mmoles) of triethylamine. Next day the reaction mixture is evaporated in vacuo, the solid residue is admixed with water, filtered, and the product is washed with water and ether. 1.26 g (92.0%) of BOC-Trp(For)-L-Ade-Asp-D-Phg-NH$_2$ are obtained; m.p.: 210° C. (decomposition), $R_f^5$: 0.45, $[\alpha]_D$: −50.5° (c: 1.0, in dimethyl formamide).

Analysis: Calculated for C$_{39}$H$_{52}$O$_9$N$_6$ (M.wt.: 748.89): C: 62.55%, H: 7.00%, N: 11.22%. Found: C: 62.52%, H: 6.81%, N: 11.38%.

Step 5
L-Tryptophyl-2-L-amino-decanoyl-aspartyl-D-phenylglycine-amide hydrochloride 1.15 g (1.53 mmoles) of BOC-Trp(For)-L-Ade-Asp-D-Phg-NH$_2$ are treated with 10 ml of 4 n hydrochloric acid in dioxane in the presence of 0.53 ml (7.5 mmoles) of mercaptoethanol. After 15 minutes the reaction mixture is evaporated in vacuo, the residue is admixed with ether, and the mixture is filtered. 0.98 g (98%) of H-Trp-L-Ade-Asp-D-Phg-NH$_2$.HCl are obtained; m.p.: 225° C. (decomposition), $R_f^7$: 0.45, $[\alpha]_D$: −47.6° (c: 1.0, in dimethyl formamide).

Step 6
tert.-Butoxycarbonyl-aminooxy-acetyl-L-tryptophyl-2-L-amino-decanoyl-L-aspartyl-D-phenylglycine-amide 0.85 g (1.24 mmoles) of H-Trp-L-Ade-Asp-D-Phg-NH$_2$.HCl are reacted with 0.55 g (1.24 mmoles) of BOC-OGly-OPCP, prepared as described in Example 1, Step 9, in 10 ml of DMF in the presence of 0.52 ml (3.72 mmoles) of triethylamine. Next day the reaction mixture is evaporated in vacuo, the residue is admixed with water, filtered, and the precipitate is washed with water and ether. The crude product, weighing 0.82 g, is subjected to chromatography on a column filled with silica gel; solvent mixture 10 is applied as eluting agent. 0.42 g of BOC-OGly-Trp-L-Ade-Asp-D-Phg-NH$_2$ are obtained; m.p.: 193°–194° C. (decomposition), $R_f^5$: 0.35, $R_f^{10}$: 0.25, $[\alpha]_D$: −35.9° (c: 1.0, in dimethyl formamide).

Analysis: Calculated for C$_{40}$H$_{55}$O$_{10}$N$_7$ (M.wt.: 793.99): C: 60.51%, H: 6.98%, N: 12.35%. Found: C: 60.54%, H: 6.87%, N: 12.16%.

EXAMPLE 12

Step 1
2-D-(tert.-Butoxycarbonyl-amino)-decanoic acid pentafluorophenyl ester One proceeds as described in Example 11, Step 1 for the preparation of the L isomer. The title compound is obtained with a yield of 75.0%; m.p.: 45°–46.5° C., $R_f^2$: 0.85, $[\alpha]_D$: +18.1° (c: 1.0, in dioxane).

Step 2
2-D-(tert.-Butoxycarbonyl-amino)-decanoyl-L-aspartyl-β-(tert.-butyl ester)-D-phenylglycine-amide 1.20 g (3.72 mmoles) of H-Asp(O$^t$Bu)-D-Phg-NH$_2$, prepared as described in Example 9, Step 2, are reacted with 1.82 g (4.0 mmoles) of BOC-D-Ade-OPFP in 10 ml of DMF in the presence of 0.56 ml (4.0 mmoles) of triethylamine. After 30 minutes the reaction mixture is evaporated in vacuo, the solid residue is admixed with ether and filtered. 1.95 g (88.8%) of BOC-D-Ade-Asp(O$^t$Bu)-D-Phg-NH$_2$ are obtained; m.p.: 156°–157° C., $R_f^4$: 0.85, $[\alpha]_D$: −47.5° (c: 1.0, in dimethyl formamide).

Analysis: Calculated for C$_{31}$H$_{50}$O$_7$N$_4$ (M.wt.: 590.74): C: 63.02%, H: 8.53%, N: 9.49%. Found: C: 63.14%, H: 8.60%, N: 9.56%.

Step 3
2-D-Amino-decanoyl-L-aspartyl-D-phenylglycine-amide hydrochloride 1.83 g (3.08 mmoles) of BOC-D-Ade-Asp(O$^t$Bu)-D-Phg-NH$_2$ are treated with 11 ml of 4 n hydrochloric acid in acetic acid. After 1 hour the reaction mixture is evaporated in vacuo, the residue is admixed with ether, and filtered. 1.45 g (99.0%) of H-D-Ade-Asp-D-Phg-NH$_2$.HCl are obtained; m.p.: 150°–153° C., $R_f^7$: 0.40, $[\alpha]_D$: −82.4° (c: 1.0, in dimethyl formamide).

Step 4
N-tert.-Butoxycarbonyl-L-tryptophyl-2-D-amino-decanoyl-L-aspartyl-D-phenylglycine-amide 1.40 g (2.97 mmoles) of H-D-Ade-L-Asp-D-Phg-NH$_2$.HCl are reacted with 1.44 g (3.05 mmoles) of BOC-Trp-OPFP in 15 ml of DMF in the presence of 1.26 ml (9.0 mmoles) of triethylamine. Next day the reaction mixture is evaporated in vacuo, the oily residue is triturated with ether in cold, and the resulting suspension is filtered. The precipitate is washed with ether, a dilute aqueous acetic acid solution and water. 1.72 g (80.4%) of BOC-Trp-D-Ade-L-Asp-D-Phg-NH$_2$ are obtained; m.p.: 170° C. (decomposition), $R_f^5$: 0.50, $[\alpha]_D$: −61.1° (c: 1.0, in dimethyl formamide).

Analysis: Calculated for C$_{38}$H$_{52}$O$_8$N$_6$ (M.wt.: 720.84): C: 63.31%, H: 7.27%, N: 11.66%. Found: C: 63.39%, H: 7.21%, N: 11.58%.

Step 5
L-Tryptophyl-2-D-amino-decanoyl-L-aspartyl-D-phenylglycine-amide hydrochloride 1.60 g (2.22 mmoles) of BOC-Trp-D-Ade-Asp-D-Phg-NH$_2$ are treated with 15 ml of 4 n hydrochloric acid in dioxane in the presence of 0.78 ml (11.1 mmoles) of mercaptoethanol. After 10 minutes the reaction mixture is evaporated, the residue is admixed with ether and filtered. 1.37 g (93.8%) of H-Trp-D-Ade-Asp-D-Phg-NH$_2$.HCl are obtained; m.p.: 243° C. (decomposition), $R_f^7$: 0.40, $[\alpha]_D$: −31.7° (c: 1.0, in dimethyl formamide).

Step 6
tert.-Butoxycarbonyl-aminooxy-acetyl-L-tryptophyl-2-D-amino-decanoyl-L-aspartyl-D-phenylglycine-amide 1.30 g (1.98 mmoles) of H-Trp-D-Ade-Asp-D-Phg-NH$_2$.HCl are reacted with 0.95 g (2.1 mmoles) of BOC-OGly-OPCP, prepared as described in Example 1, Step 9, in 15 ml of DMF in the presence of 0.84 ml (6.0 mmoles) of triethylamine. Next day the reaction mixture is evaporated in vacuo, and the oily residue is triturated with water. The resulting suspension is filtered and the precipitate is washed with a dilute aqueous solution of acetic acid. Thereafter the crude product is crystallized from 80% ethanol. 0.96 g (61.2%) of BOC-OGly-Trp-D-Ade-Asp-D-Phg-NH$_2$ are obtained; m.p.:

200°–203° C. (decomposition), $R_f^5$: 0.45, $[\alpha]_D$: −26.9° (c: 1.0, in dimethyl formamide).

Analysis: Calculated for $C_{40}H_{55}O_{10}N_7$ (M.wt.: 793.99): C: 60.51%, H: 6.98%, N: 12.35%. Found: C: 60.50%, H: 6.50%, N: 12.19%.

What we claim is:

1. A peptide of formula (I), $$A\text{-Trp-}B\text{-Asp-Phg-}NH_2 \qquad (I)$$

wherein

A is tert.-butoxycarbonyl-aminooxy-acyl, benzyloxycarbonyl-aminooxy-acyl, (aminooxy)-acyl or E-aminooxy-acyl, wherein E is benzoyl or a straight-chained or branched $C_{1-5}$ aliphatic acyl, and B is methionyl, leucyl, norleucyl, norvalyl or 2-aminodecanoyl, or an acid addition salt or complex thereof.

2. α-(tert.-Butoxycarbonyl-aminooxy)-acetyl-L-tryptophyl-L-methionyl-L-aspartyl-D-phenylglycine-amide.

3. α-(tert.-Butoxycarbonyl-aminooxy)-acetyl-L-tryptophyl-L-methionyl-L-aspartyl-L-phenylglycine-amide.

4. α-D-(tert.-Butoxycarbonyl-aminooxy)-propionyl-L-tryptophyl-L-methionyl-L-aspartyl-D-phenylglycine-amide.

5. α-D-(tert.-Butoxycarbonyl-aminooxy)-propionyl-L-tryptophyl-L-methionyl-L-aspartyl-L-phenylglycine-amide.

6. α-(tert.-Butoxycarbonyl-aminooxy)-acetyl-L-tryptophyl-L-leucyl-L-aspartyl-D-phenylglycine-amide.

7. α-(tert.-Butoxycarbonyl-aminooxy)-acetyl-L-tryptophyl-L-leucyl-L-aspartyl-L-phenylglycine-amide.

8. α-D-(tert.-Butoxycarbonyl-aminooxy)-propionyl-L-tryptophyl-L-leucyl-L-aspartyl-D-phenylglycine-amide.

9. α-D-(tert.-Butoxycarbonyl-aminooxy)-propionyl-L-tryptophyl-L-leucyl-L-aspartyl-L-phenylglycine-amide.

10. α-D-(tert.-Butoxycarbonyl-aminooxy)-propionyl-L-tryptophyl-L-norleucyl-L-aspartyl-D-phenylglycine-amide.

11. α-D-(tert.-Butoxycarbonyl-aminooxy)-propionyl-L-tryptophyl-L-norvalyl-L-aspartyl-D-phenylglycine-amide.

12. α-tert.-Butoxycarbonyl-aminooxy-acetyl-L-tryptophyl-2-L-amino-decanoyl-L-aspartyl-D-phenylglycine-amide.

13. α-tert.-Butoxycarbonyl-aminooxy-acetyl-L-tryptophyl-2-D-amino-decanoyl-L-aspartyl-D-phenylglycine-amide.

14. A pharmaceutical diagnostic composition containing an effective amount of a compound according to claim 1, or a pharmaceutically acceptable salt or complex thereof, with a pharmaceutical adjuvant and/or auxiliary agent.

15. A process for the diagnosis of gastric activity which comprises the steps of administration to diagnostic subjects an effective amount of a composition according to claim 14 and measuring the resultant change in gastric acidity.

16. The compound according to claim 1 wherein the peptide is selected from the group consisting of:

α-(tert.-Butoxycarbonyl-aminooxy)-acetyl-L-tryptophyl-L-methionyl-L-aspartyl-D-phenylglycine-amide;
α-(tert.-Butoxycarbonyl-aminooxy)-acetyl-L-tryptophyl-L-methionyl-L-aspartyl-L-phenylglycine-amide;
α-D-(tert.-Butoxycarbonyl-aminooxy)-propionyl-L-tryptophyl-L-methionyl-L-aspartyl-D-phenylglycine-amide;
α-D-(tert.-Butoxycarbonyl-aminooxy)-propionyl-L-tryptophyl-L-methionyl-L-aspartyl-L-phenylglycine-amide;
α-(tert.-Butoxycarbonyl-aminooxy)-acetyl-L-tryptophyl-L-leucyl-L-aspartyl-D-phenylglycine-amide;
α-(tert.-Butoxycarbonyl-aminooxy)-acetyl-L-tryptophyl-L-leucyl-L-aspartyl-L-phenylglycine-amide;
α-D-(tert.-Butoxycarbonyl-aminooxy)-propionyl-L-tryptophyl-L-leucyl-L-aspartyl-D-phenylglycine-amide;
α-D-(tert.-Butoxycarbonyl-aminooxy)-propionyl-L-tryptophyl-L-leucyl-L-aspartyl-L-phenylglycine-amide;
α-D-(tert.-Butoxycarbonyl-aminooxy)-propionyl-L-tryptophyl-L-norleucyl-L-aspartyl-D-phenylglycine-amide;
α-D-(tert.-Butoxycarbonyl-aminooxy)-propionyl-L-tryptophyl-L-norvalyl-L-aspartyl-D-phenylglycine-amide;
α-tert.-Butoxycarbonyl-aminooxy-acetyl-L-tryptophyl-2-L-amino-decanoyl-L-aspartyl-D-phenylglycine-amide; and
α-tert.-Butoxycarbonyl-aminooxy-acetyl-L-tryptophyl-2-D-amino-decanoyl-L-aspartyl-D-phenylglycine-amide.

* * * * *